US006919919B2

(12) United States Patent
Nelson et al.

(10) Patent No.: US 6,919,919 B2
(45) Date of Patent: Jul. 19, 2005

(54) LIGHT CALIBRATION DEVICE FOR USE IN LOW LEVEL LIGHT IMAGING SYSTEMS

(75) Inventors: Michael B. Nelson, San Fancisco, CA (US); Bradley Rice, Danville, CA (US); Brian R. Bates, Lafayette, CA (US); Barton V. Beeman, San Mateo, CA (US)

(73) Assignee: Xenogen Corporation, Alameda, CA (US)

( * ) Notice: Subject to any disclaimer, the term of this patent is extended or adjusted under 35 U.S.C. 154(b) by 528 days.

(21) Appl. No.: 10/068,573

(22) Filed: Feb. 6, 2002

(65) Prior Publication Data

US 2003/0146663 A1 Aug. 7, 2003

(51) Int. Cl.[7] .............................................. H04N 17/00
(52) U.S. Cl. ...................... 348/187; 348/82; 348/216.1
(58) Field of Search .......................... 348/187, 82, 188, 348/216.1; 600/409, 476; 702/27, 81; 424/9.6; 435/4

(56) References Cited

U.S. PATENT DOCUMENTS

| 4,196,994 | A | * | 4/1980 | de Jesus et al. ............. 396/133 |
|---|---|---|---|---|
| 4,948,975 | A | * | 8/1990 | Erwin et al. ............. 250/361 C |
| 5,202,091 | A | | 4/1993 | Lisenbee ...................... 422/52 |
| 5,319,209 | A | | 6/1994 | Miyakawa et al. ....... 250/459.1 |
| 5,414,258 | A | | 5/1995 | Liang ....................... 250/252.1 |
| 5,636,299 | A | | 6/1997 | Bueno et al. .................. 385/15 |
| 5,637,874 | A | | 6/1997 | Honzawa et al. ....... 250/361 C |
| 5,650,135 | A | | 7/1997 | Contag et al. ................ 424/9.1 |
| 5,672,881 | A | | 9/1997 | Striepeke et al. ........ 250/461.2 |
| 5,705,807 | A | | 1/1998 | Throngnumchai et al. ........................ 250/214 P |
| 5,738,101 | A | | 4/1998 | Sappey ....................... 128/665 |
| 5,840,572 | A | | 11/1998 | Copeland et al. ......... 435/286.7 |
| 5,867,250 | A | | 2/1999 | Baron ......................... 351/212 |
| 5,970,164 | A | | 10/1999 | Bamberger et al. .......... 382/128 |
| 6,205,244 | B1 | * | 3/2001 | Bawolek et al. ............. 382/162 |
| 6,217,847 | B1 | | 4/2001 | Contag et al. ................ 424/9.1 |
| 6,242,743 | B1 | | 6/2001 | DeVito et al. .......... 250/363.05 |
| 6,321,111 | B1 | | 11/2001 | Perelman et al. ............ 600/477 |
| 6,364,829 | B1 | | 4/2002 | Fulghum ..................... 600/160 |
| 6,615,063 | B1 | | 9/2003 | Ntziachristos et al. ....... 600/312 |
| 6,642,953 | B1 | * | 11/2003 | Nieto Velasco et al. ....... 348/61 |
| 6,775,567 | B2 | | 8/2004 | Cable et al. ................. 600/407 |
| 2001/0028510 | A1 | * | 10/2001 | Ramm et al. ................ 359/663 |
| 2003/0156194 | A1 | * | 8/2003 | Sugiura et al. .............. 348/187 |

FOREIGN PATENT DOCUMENTS

WO     WO 00/17643     3/2000     ........... G01N/33/53

OTHER PUBLICATIONS

Integrated Photomatrix Limited, "Closed Loop Control", Dorset, England, available Dec. 1, 2001.

Dynex Technologies, Inc., website, A Thermo BioAnalysis Company "Dynex Microplates", http://www.dynextechnologies.com/index.html, printed Apr. 19, 2002.

(Continued)

Primary Examiner—Victor R. Kostak
(74) Attorney, Agent, or Firm—Beyer Weaver & Thomas LLP

(57) ABSTRACT

The invention describes systems and methods for calibrating a low-level light imaging system. Techniques described herein employ a light calibration device that is placed within a low level light imaging box to calibrate the system and its constituent components such as the camera and processing system. The calibration device comprises an array of low-power light supplies each having a known emission. By taking an image of each low-power light supply, and comparing the processed result with the known emission, the accuracy of the imaging system and its absolute imaging characteristics may be assessed and verified.

30 Claims, 7 Drawing Sheets

OTHER PUBLICATIONS

Optronic Labroatories, Inc., website, Manufacturer of Light Measurement Instrumentation, Standards, http://olinet.com/, printed Apr. 19, 2002.

Labsphere, website http://labsphere.com, printed Apr. 19, 2002.

Lambda Research Corporation, website, http://lambdares.com, printed Apr. 19, 2002.

Hamamatsu Corporation, USA, website, http://usa.hamamatusu.com/ pp. 1–4, Apr. 27, 2001, printed on Apr. 27, 2001.

Hamamatsu, Imaging Box Instruction Manual, 55310–224–1, Nov. 2000.

* cited by examiner

LIGHT CALIBRATION DEVICE FOR USE IN LOW LEVEL LIGHT IMAGING SYSTEMS

FIELD OF THE INVENTION

The present invention relates generally to calibration techniques. More specifically, the present invention relates to calibration techniques suitable for use in low level light imaging systems capable of imaging low intensity light sources.

BACKGROUND OF THE INVENTION

One new and specialized type of imaging involves the capture of low intensity light—often on the order of only tens to hundreds of photons—from a light emitting sample. The source of the light indicates portions of the sample, such as traced molecules in a particular portion of a laboratory mammal, where an activity of interest may be taking place. For example, specialized in-vivo imaging applications may include analysis of one or more representations of emissions from internal portions of a specimen superimposed on a photographic representation of the specimen. The luminescence representation indicates portions of the specimen where an activity of interest may be taking place. The photographic representation provides the user with a pictorial reference of the specimen. Such imaging applications present numerous challenges.

One particular obstacle for these imaging systems is the diverse image capture conditions that they are required to perform under. Photographic image capture typically requires the sample to be fully illuminated. Luminescent image capture requires substantially no light, other than minute amounts produced within the sample. The accuracy of image capture at these low light levels is often inconsistent with conventional imaging systems. For example, inconsistency between different camera designs may affect the accuracy between different imaging systems. Alternately, drift introduced in the readout of a camera over its operational life may introduce inaccuracies that affect the repeatability of imaging within the same system over time. Irregularities between image capture trials on the order of several photons may contaminate data; thereby compromising the ability for an imaging system to provide absolute and repeatable results.

Since the cameras employ considerable sensitivity at low light levels, conventional techniques for calibration often produce too much light, saturate the cameras, and are unsuitable. In view of the foregoing, techniques for calibrating a low-level light imaging system would be desirable.

SUMMARY OF THE INVENTION

The present invention relates to systems and methods for calibrating a low-level light imaging system. Techniques described herein employ a light calibration device that is placed within a low level light imaging box to calibrate the system and its constituent imaging components such as the camera, imaging box and lens. The calibration device comprises an array of low-emission light supplies having a known emission. In one embodiment, the array of low-emission light supplies are Lambertian surface emitters with a surface radiance of between about $10^3$ to about $10^{10}$ photons/second/centimeter squared/steradian. By taking an exposure of one or more of the low-power light sources, and comparing the processed result with the known emission, the accuracy of the imaging system and its absolute imaging characteristics may be assessed and verified.

In one aspect, the present invention relates to a calibration device for calibrating an imaging system. The imaging system is responsible for capturing an image of a low intensity light source. The device comprises an array of low intensity light supplies for emitting light in the range of about $10^3$ to about $10^{10}$ photons/second/centimeter squared/steradian. Each low intensity light supply comprises a light interface for receiving light from a light source and to emit at least a portion of the light from the device. The device also comprises a housing that contains the array of low intensity light supplies. The device further comprises a voltage source, in electrical communication with the light source for each low intensity light supply, and designed or configured to provide power to the light source.

In another aspect, the present invention relates to a system for capturing an image of a low intensity light source with a camera. The system comprises an imaging box having a set of walls enclosing an interior cavity and a camera mount configured to position the camera relative the interior cavity. The system further comprises a calibration device including a voltage source and an array of low intensity light supplies. The low intensity light supplies may emit light in the range of about $10^3$ to about $10^{10}$ photons/second/centimeter squared/steradian. Each low intensity light supply comprises a light interface for receiving light from a light source and to emit at least a portion of the light from the device. The voltage source is in electrical communication with the light source for each low intensity light supply. The system additionally comprises a processor designed or configured to receive image data corresponding to light emitted from the calibration device and compare the image data to known light emission data for the calibration device.

In yet another aspect, the present invention relates to a method for calibrating a system capable of capturing an image of a low intensity light source. The system comprises an imaging box and a camera for capturing the image. The method comprises placing a light calibration device in the imaging box, the light calibration device including an array of low intensity light supplies. The method also comprises emitting light from one or more of the low intensity light supplies in the range of about $10^3$ to about $10^{10}$ photons/second/centimeter squared/steradian. The method further comprises receiving the light from the one or more of the low intensity light supplies using the camera. The method additionally comprises comparing the received light with a known light emission for the one or more of the low intensity light supplies.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

I. Imaging System

Figure 1:
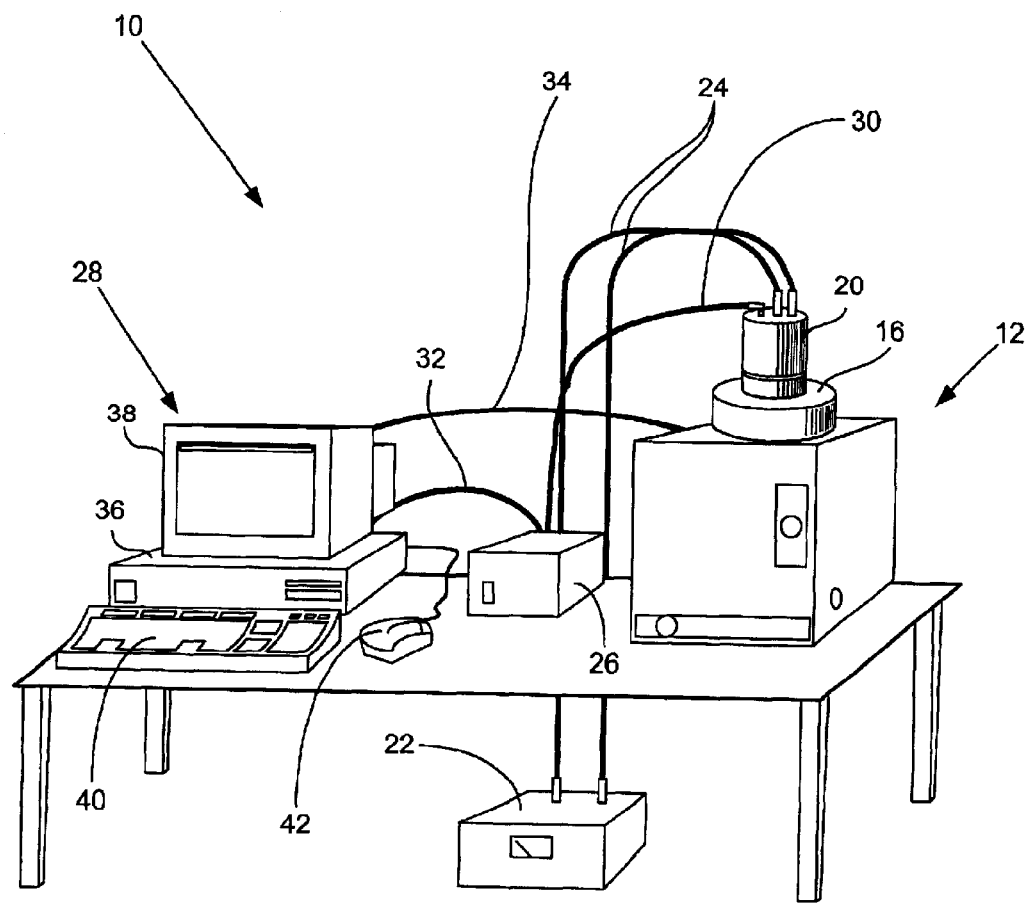
FIG. 1 is a perspective view of an imaging system in accordance with one embodiment of the present invention.

In one aspect, the present invention relates to imaging systems for capturing an image of a low intensity light source. FIG. 1 illustrates an imaging system 10 configured to capture photographic and luminescence images in accordance with one embodiment of the present invention. Imaging system 10 may be used for imaging a low intensity light source, such as luminescence from luciferase-expressing cells, fluorescence from fluorescing molecules, and the like. The low intensity light source may be emitted from any of a variety of light-emitting samples which may include, for example, tissue culture plates, multi-well plates (including 96, 384 and 864 well plates), and animals or plants containing light-emitting molecules, such as various mammalian subjects such as mice containing luciferase expressing cells.

Imaging system 10 comprises an imaging box 12 having a door and walls that define an interior cavity that is adapted to receive a light-emitting sample in which low intensity light, e.g., luciferase-based luminescence, is to be detected. The calibration device of FIG. 3 may also be placed within box 12. Imaging box 12 is suitable for imaging including the capture of low intensity light on the order of individual photons, for example. Imaging box 12 is often referred to as "light-tight", e.g., it seals out essentially all of the external light from the ambient room from entering the box 12, and may include one or more seals that prevent light passage into the box when the door is closed.

Imaging box 12 includes an upper housing 16 adapted to receive a camera. A high sensitivity camera 20, e.g., an intensified or a charge-coupled device (CCD) camera, is mounted on top of upper housing 16 and positioned above imaging box 12. The CCD camera 20 is capable of capturing luminescent and photographic (i.e., reflection based images) images of a sample or calibration device placed within imaging box 12. The CCD camera 20 is cooled by a suitable source such as a refrigeration device 22 that cycles a cryogenic fluid through the CCD camera via conduits 24. A suitable refrigeration device is the "CRYOTIGER" compressor, which can be obtained from IGC-APD Cryogenics Inc., Allentown, Pa. Other methods, such as liquid nitrogen, may be used to cool the CCD camera 20.

An image processing unit 26 optionally interfaces between camera 20 and a computer 28 through cables 30 and 32 respectively. Computer 28, which may be of any suitable type, typically comprises a main unit 36 that typically contains hardware including a processor, memory components such as random-access memory (RAM) and read-only memory (ROM), and disk drive components (e.g., hard drive, CD, floppy drive, etc.). Computer 28 also includes a display 38 and input devices such as a keyboard 40 and mouse 42. Computer 28 is in communication with various components in imaging box 12 via cable 34. To provide communication and control for these components, computer 28 includes suitable processing hardware and software configured to provide output for controlling any of the devices in imaging box 12. The processing hardware and software may include an I/O card, control logic for controlling any of the components of imaging system 10, and a suitable graphical user interface that facilitates user interaction with imaging system 10. Components controlled by computer 28 may include camera 20, the motors responsible for camera 20 focus, the motors responsible for position control of a platform supporting the sample, the camera lens, f-stop, etc.

Computer 28 may also include suitable processing hardware and software for camera 20 such as additional imaging hardware and software, calibration software, and image processing logic for processing information obtained by camera 20. For example, a processor in computer 28 may be designed or configured to receive image data corresponding to light emitted from a calibration device and compare the image data to known light emission data for the calibration device. The logic in computer 28 may take the form of software, hardware or a combination thereof. Computer 28 also communicates with a display 38 for presenting imaging information to the user. For example, the display 38 may be a monitor, which presents an image measurement graphical user interface (GUI) that allows the user to view imaging results and also acts an interface to control the imaging system 10.

II. Calibration Device

Figure 2A:
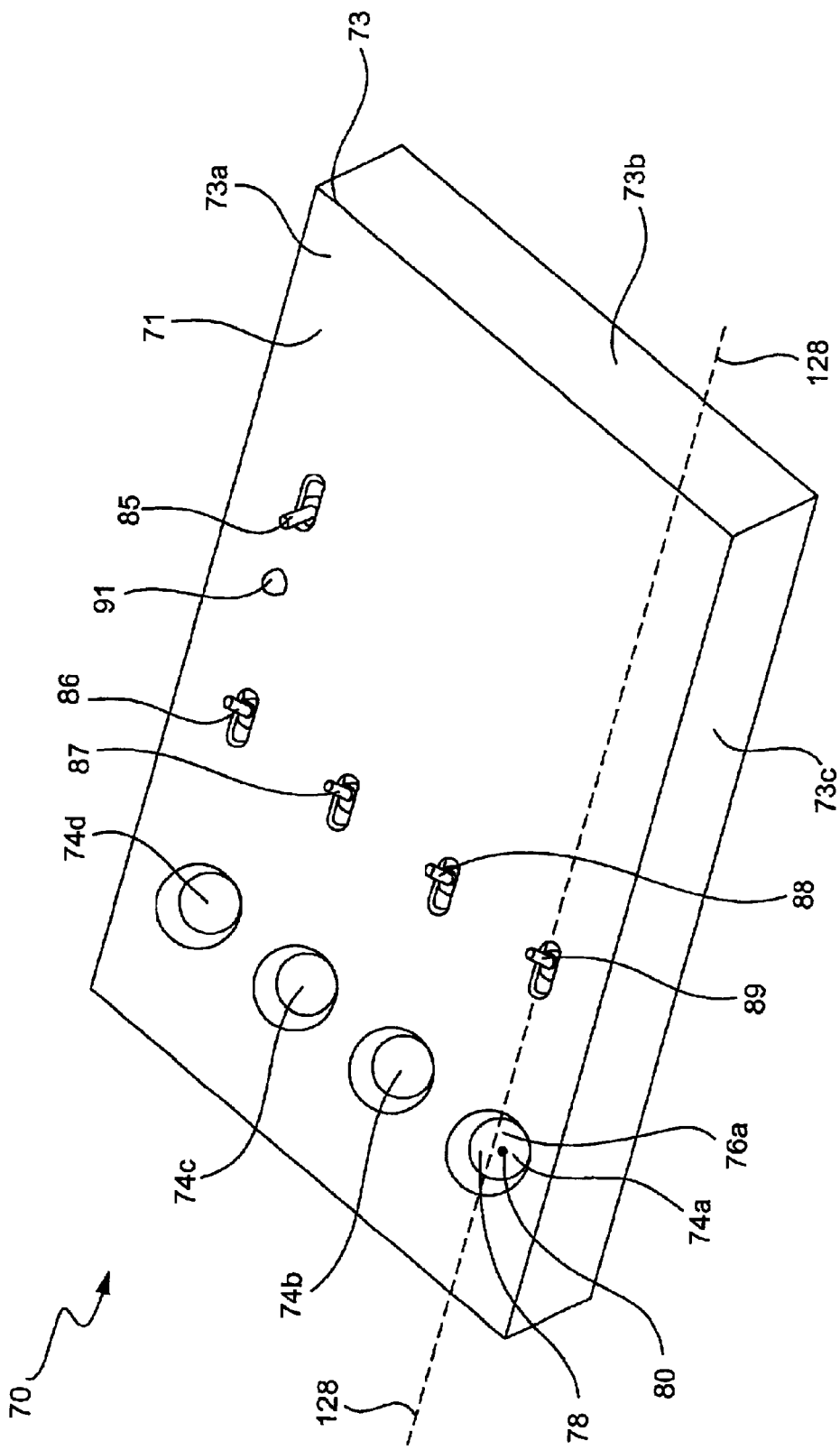
FIGS. 2A–2B illustrate different views of a light calibration device in accordance with one embodiment of the present invention.
Figure 2B:
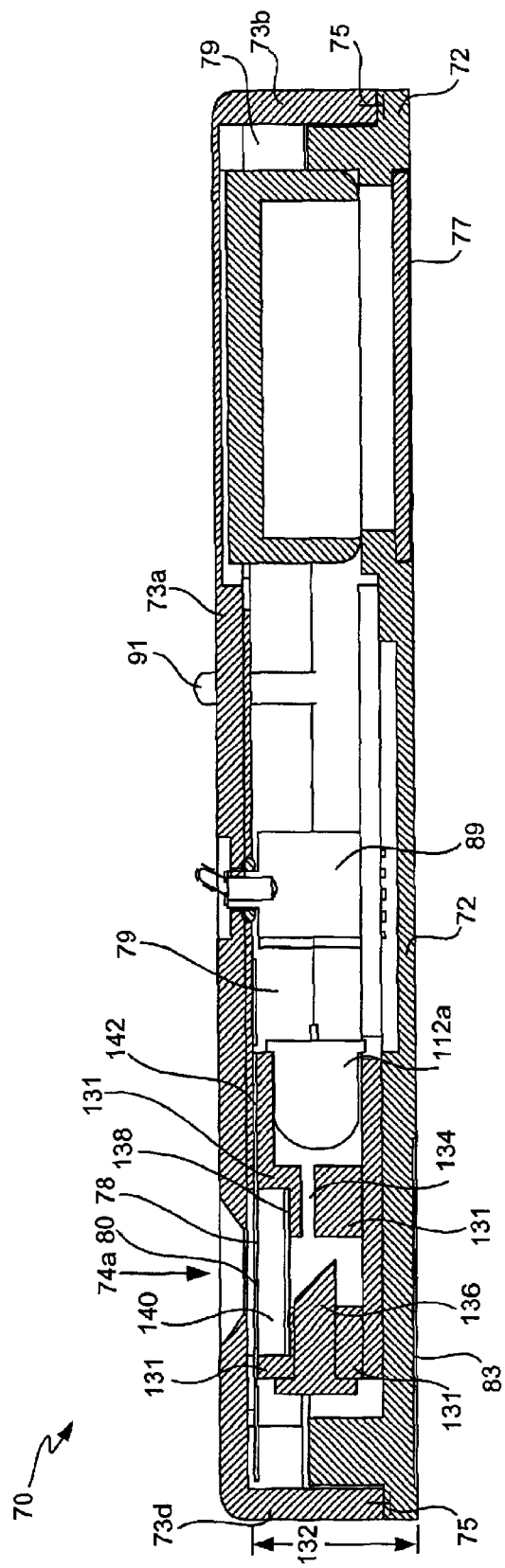

The present invention employs a discrete device to assist calibration of a low level light imaging system. FIGS. 2A–2B illustrate a light calibration device 70 in accordance with one embodiment of the present invention. Calibration device 70 includes an array of low intensity light supplies 74a–d held by a housing 71.

Referring to FIGS. 2A and 2B, housing 71 provides mechanical integrity for device 70 and protects electronic components contained therein. In a specific embodiment, housing 71 comprises two pieces of machined aluminum fixed together. The first piece, containment piece 73, comprises a top 73a and four sidewalls 73b–73e which form an interior cavity 79 (FIG. 2B) in which electronic components are contained. In the embodiment where housing 71 comprises machined aluminum pieces, containment piece 73 is machined from a single block of black anodized aluminum to form sidewalls 73b–73e and top 73a, which define interior cavity 79. A matching faceplate 72 (FIG. 2B) mates with the bottom walls of containment piece 73 such that the device 70 is substantially "light-tight", e.g., it prevents essentially all of the light produced within the interior 79 from escaping housing 71 other than through the array of low intensity light supplies 74. To facilitate the light-tight nature of device 70, one or more gaskets or seals may be disposed at the mating interface of containment piece 73 and faceplate 72. For example, the gasket may comprises a sheet of adhesive backed neoprene rubber with peel off paper backing cut to size of the mating interface and cut to accommodate holes for each light source. Screws 75 detachably fix faceplate 72 to containment piece 73. Faceplate 72 also comprises a removable battery hatch 77 that allows a user access to a battery cavity within device 70. Sticker 83 is attached to faceplate 72 and provides light calibration information for each light supply 74. For example, the information may include absolute photon emission over time, e.g. the number of photons per second, for each light supply 74.

Each light supply 74 emits consistent and low-intensity light from device 70. As the term is used herein, a low intensity light supply of the present invention emits light in the range of about $10^3$ to about $10^{10}$ photons/second/centimeter squared/steradian. For some imaging systems, a low intensity light supply that emits light in the range of about $10^5$ to about $10^7$ photons/second/centimeter squared/steradian is suitable for calibration. The allowable range for light emitted from each light supply 74a–74d will depend on a number of factors such as the sensitivity and saturation of the camera used, the ability of the imaging box to seal light, level of internally generated light in the imaging box, imaging system parameters such as integration time, binning, and f-stop, etc. In one embodiment, the intensity of light emitted from a light supply 74 may be determined according to the sensitivity of a camera used in the imaging system over a duration corresponding to saturation of the camera caused by light emitted from the light supply 74. Saturation refers to the amount of light and time it takes for the camera, or the analog-to-digital converter associated with the camera, to reach its exposure capacity. For example, the saturation duration may range from about five seconds to about five minutes, depending on the rate of light emitted from the object.

Each light supply 74 comprises a light source that generates light. In one embodiment, the array of light supplies 74 is 'discrete' in that each light supply 74 receives light from a single light source dedicated to an individual light supply. Since most conventional light sources produce too much light and may saturate a low-level light imaging system, the light produced from the light source may be reduced in intensity before emission from each light supply 74. To reduce the intensity of light produced from each light source and to control the light emitted from device 70, each light supply 74 comprises a light interface 76 for receiving light from a light source and emitting at least a portion of the light from the device 70.

For example, light supply 74a comprises a light interface 76a that facilitates spatial calibration for an imaging system. Light interface 76a includes an opaque diaphragm 78 having a light transmission pinhole 80. In one embodiment, pinhole 80 has a known and tightly toleranced diameter such that light emitted from light supply 74a, received by a camera, and processed by an imaging system, produces an image whose diameter may be compared with the known diameter of pinhole 80. This may be advantageous to assess imaging system, or camera, spatial integrity for detecting the size of imaged objects. For example, spatial calibration using light supply 74a is suitable to detect the presence of any 'bleed' between channels of a camera. Pinhole 80 diameters in the range of 10 microns to about 100 microns are suitable for many applications. Alternately, pinhole 80 diameters in the range of about 30 to about 100 microns may be suitable. In a specific embodiment, diaphragm 78 is aluminum and pinhole 80 is machined using laser drilling or other suitable tightly toleranced machining techniques.

Light supply 74a is also suitable for assessing the spatial integrity between photographic and luminescent image capture for an imaging system. For example, an overlay image comprising a combination of a luminescent image of device 70 disposed overtop a photographic image of device 70 will readily indicate spatial inconsistencies of the location of pinhole 80 between the luminescent image and the photographic image. The offset may then be used to calibrate the system or alleviate the inconsistency.

Light supplies 74b–74d emit light that enables spectral calibration. More specifically, light supply 74b emits green light of a known wavelength, light supply 74c emits red light of a known wavelength and a relatively low intensity, and light supply 74d emits red light of a known wavelength and a higher intensity than that of light supply 74c. Since the spectral resolution of many CCD cameras may diminish at the borders of the visible light spectrum, light supplies 74b–74d may be used to assess the spectral integrity of the imaging system within, and at the extremes, of the visible light spectrum. Light received by a camera, and processed by an associated imaging system, may produce an image whose spectral characteristics are compared to known spectral emissions for light supplies 74b–74d.

Light supply 74c and light supply 74d emit a low intensity and high-intensity relative to each other. In a specific embodiment, light supply 74c emits light in the range of about $10^3$ to about $10^5$ photons/second/centimeter squared/steradian while light supply 74d emits light in the range of about $10^7$ to about $10^9$ photons/second/centimeter squared/steradian. Again, the amount of light emitted from each light source may vary based on a particular camera and system being calibrated.

Device 70 also comprises a series of switches 85–90. Switch 85 acts as a master on/off switch for device 70 and allows the user to turn on/off all the light supplies 74 simultaneously. Status indicator 91 indicates operation of device 70. In one embodiment, status indicator 91 temporally flashes to indicate operation of device 70 so as to not overwhelm light emitted from the low intensity light supplies 74 during calibration. A conventional off-the-shelf diode may be suitable to temporarily produce light for status indicator 91. Switches 86–89 allow separate on/off control for each light supply 74. More specifically, switch 86 allows individual on/off control of light supply 74d, switch 87 allows individual on/off control of light supply 74c, switch 88 allows individual on/off control of light supply 74b, and switch 89 allows individual on/off control of light supply 74a.

Figure 3:
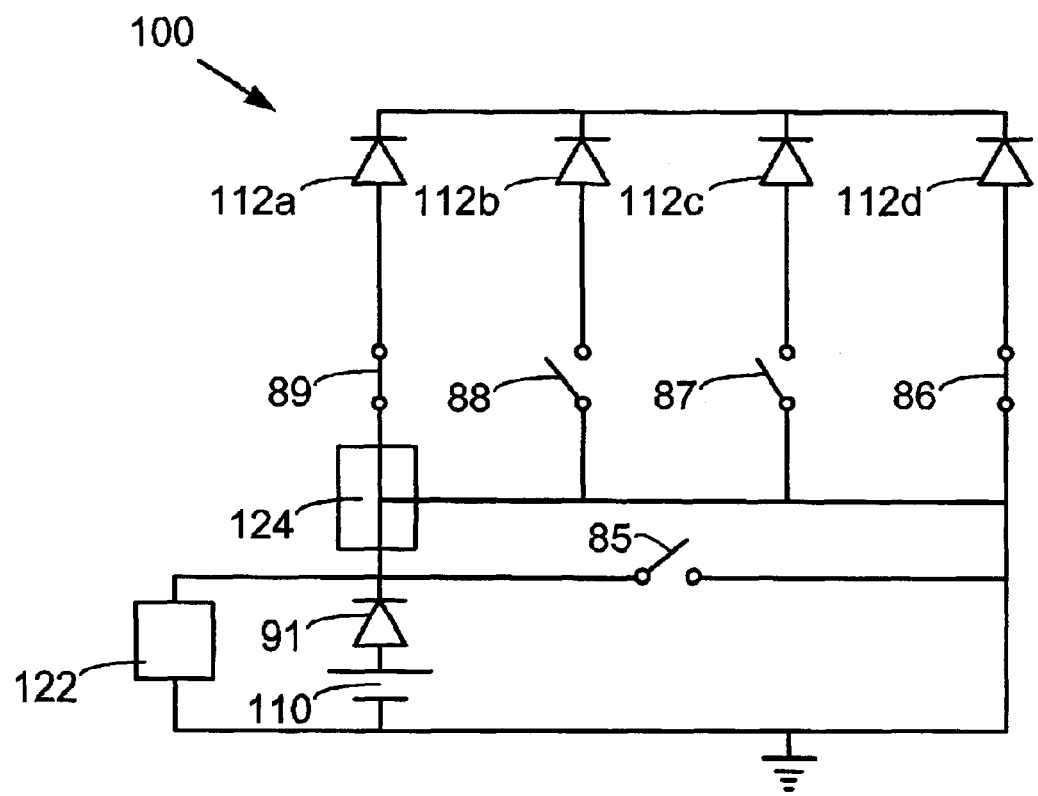
FIG. 3 illustrates an electrical schematic of the light calibration device of FIG. 3 in accordance with a specific embodiment of the present invention.

FIG. 3 illustrates an electrical schematic 100 of light calibration device 70 in accordance with a specific embodiment of the present invention. As shown, calibration device 70 includes voltage source 110, light sources 112, switches 85–89, voltage shut off 122, status indicator 91, and voltage regulator 124.

Voltage source 110 is in electrical communication with light sources 112 and provides voltage and power to electrical components employed within calibration device 70. In a specific embodiment, voltage source 110 comprises between 1 and 5 conventional AAA batteries.

Light sources 112a–d generate light. As will be described in greater detail with respect to FIG. 2B, much of the light generated by light sources 112 is not emitted from device 70, but instead is reduced in intensity to achieve low intensity light levels desirable for many specialized imaging applications. In one embodiment, light sources 112a–d each comprise a low intensity diode. A low intensity diode model number IPL1060630JAL as produced by Integrated Photomatrix of Dorchester, Dorset, England may be suitable as a light source for use within calibration device 70.

Device 70 may include electrical components to facilitate substantially consistent light output over the operating life of the calibration device. In a specific embodiment, light sources 112a–d are self-monitoring in that the light sources are designed or configured to monitor the amount of light generated therefrom and adapt the amount of light to maintain substantially consistent light output from device 70. More specifically, the output from the monitoring diode may be used to control the current flowing to the LED, in order to maintain a constant light level, irrespective of aging or temperature effects. The receiving detector may be used to give an absolute indication of transmissivity through the medium, since the light level is held constant. Using self-monitoring light sources in this manner allows device 70 to accommodate minor fluctuations in temperature or voltage without sacrificing consistent light output.

Device 70 may also include additional electrical components to facilitate substantially consistent light output over the operating life of the calibration device. For example, a voltage shut off 122 may be disposed in electrical communication with voltage source 110. Voltage shut off 122 terminates voltage provided by voltage source 110 to light sources 112a–d when the voltage provided by voltage source 110 becomes insufficient to produce allowable light output from light supplies 74, e.g., due to battery age. In addition, device 70 may include a voltage regulator 124 in electrical communication with voltage source 110. Voltage regulator 124 controls the voltage and current provided to each light source 112.

Referring to FIG. 2B, a side perspective view of calibration device 70 is illustrated along dashed line 128 of FIG. 2A. Device 70 comprises an optic block 131 that holds the light generation and light interface components of device 70. Optic block is fixed to housing 71. As shown, FIG. 2B illustrates light supply 74a of FIG. 2A and its constituent light source 112a and light interface. In this case, the light interface for light supply 74a comprises channel 134, deflection interface 136, neutral density filter 138, diffuser 140, and several other components to reduce the amount of light emitted from device 70.

As shown in FIG. 2B, light source 112a comprises a low intensity diode disposed on its side in order to reduce the height 132 of device 70. As will be described below, the height 132 of device 70 may be limited in some cases based on the depth of field of focus of an imaging system that device 70 is employed with. Light emitted from light source 112a passes substantially horizontally through light channel 134 and strikes deflection interface 136. Deflection interface 136 deflects light emitted horizontally by light source 112a and directs a portion of the light upward for emission from device 70. In one embodiment, the surface of deflection interface 136 facing light source 112a is angled upward to increase the amount of light directed upward. Alternately, the surface of deflection interface 136 may be vertical and perpendicular to the direction of light emitted from light source 112a, thereby reducing the amount of light reflected and producing a more Lambertian reflection. Deflection interface 136 may be constructed of Teflon, for example. In another embodiment, a mirror or otherwise suitably reflective surface may be attached to deflection interface 136 to increase, or otherwise control, the amount of light transmitted from light source 112a upwards.

Disposed along a light path between light source 112a and emission of light from light supply 74a is neutral density filter 138. Thus, light transmitted upwards by deflection interface 136 passes through neutral density filter 138. Neutral density filter 138 attenuates—or reduces the intensity of—light transmitted through filter 138 across all wavelengths. In some designs, a neutral density filter 138 is disposed to control the output intensity of light emitted from each light supply 74. In a specific embodiment, neutral density filter 138 comprises a stack of 2–4 different filters. For example, a neutral density filter model number K53-706 as produced by Kodak of Rochester, N.Y. is suitable for use within calibration device 70.

Disposed along a light path between light source 112a and emission of light from light supply 74a is diffuser 140. Diffuser 140 diffuses, or otherwise affects or controls, light emitted from light supply 74a. Diffuser 140 effectively establishes light supply 74a as a surface emitter. In one embodiment, diffuser 140 converts relatively focused or directional light reflected from deflection interface 136 into substantially Lambertian light emitted from light supply 74a. In this manner, calibration using device 70 reduces dependency on the position of calibration device 70 within imaging box 12 relative to the camera. In some cases, diffuser 140 allows light emitted from device 70 to form a particular pattern. In a specific embodiment, diffuser 140 includes an opalized surface that is particularly effective for creating a Lambertian distribution. For example, a diffuser model number L46-105 as produced by Edmund Industrial Optics of Barrington, N.J. is suitable for use within calibration device 70.

Retainer 142 holds diffuser 140 to optic block 131 and is attached to the optic block 131, e.g., using screws. Retainer 142 also includes a central portion, disposed between light source 112a and emission of light from light supply 74a, that includes the opaque diaphragm 78 and pinhole 80 described above with respect to FIG. 2A. In one embodiment, the size of pinhole 80 is used to control the amount of light emitted from light supply 74. Thus, any one or more of the interface components—e.g., diffuser 140, neutral density filter 138, and pinhole 80—may be used to control the intensity of light emitted from one of the light supplies 74a–d of FIG. 2A. Since the emission characteristics of each component is known before assembly of device 70, this allows a limited set of pre-manufactured components to be flexibly selected during device 70 manufacture to obtain a custom light emission for each light supply. Component selection in this manner enables simple, flexible, and modular manufacturing techniques to produce light calibration devices with light sources each having a custom light emission.

Height 132 is defined as the distance from the bottom cover to the top of the emitting surface for each light source. In one embodiment, height 132 is configured relative to the depth of field of focus of an imaging system that the device 70 is used with. Alternately, height 132 maybe designed relative to the average height of a surface of a specimen to be imaged. It is understood that the depth of field of focus for an imaging system will vary depending on several parameters, and vary with the type of imaging performed in the system (e.g., camera characteristics and continual imaging of the top surface of a mammalian specimen is then dependent on the mammal); and the height 132 of calibration device 70 may be tailored accordingly. A calibration device having a height between about 5 mm to about 30 mm is suitable for many imaging systems. In a specific embodiment, height 132 is about 15 mm, which corresponds to the average height of a mammalian specimen commonly used in imaging applications. Calibration device 70 as shown in FIG. 2B has a height 132 of about 15 mm.

While the present invention has been described with respect to a particular light source arrangement for calibration device 70, is understood that the number of light sources 74, and the frequency and intensity of light emitted from each light source, may depend on a particular application. For example, while calibration device 70 has been described with respect to four light supplies 74, is understood that calibration device 70 may include an array of light supplies ranging from 1 to 64 light supplies, as desired for calibrating a particular imaging system. For many imaging systems, 2–8 light supplies are sufficient. In one design, calibration device 70 includes four light supplies, each having a light intensity an order of magnitude larger than its neighbor. This design is particularly advantageous to compare the sensitivity of different imaging systems. More specifically, a low quality imaging system may only be able to detect the fourth light supply having the largest intensity while a high quality imaging system will be able to detect all four light supplies. Alternately, calibration device 70 may comprise four light supplies each having a different spectral frequency. For example, four conventional light emmitting diodes each having an emission frequency in between 425 and 950 nanometers may be used. This design is particularly well-suited to calibrate and assess the spectral characteristics and integrity of an imaging system.

In one embodiment, calibration device 70 includes a linear array of light supplies 74 that extend the focal radius of a camera. Calibration using this device is particularly well-suited to measure flat field correction of a camera. Flat field correction of a camera refers to calibration corrections factored into imaging due to camera lens curvature at the lens periphery. In this case, the linear array may comprise 16 light supplies that span the radius of a camera lens, for example.

III. Operation of an Imaging System

The present invention may be used for a wide variety of imaging applications. Generally, the present invention may be used with systems that employ any non-invasive methods and compositions for detecting, localizing and tracking light-emitting entities and biological events in a mammalian subject. For example, the imaging system 10 of FIG. 1 and calibration device 70 may be implemented with intensified Charge-Coupled Device (CCD) cameras to detect the localization of light-producing cells (e.g., certain bacteria or tumor cells made bioluminescent by transforming them with luciferase DNA constructs) inside of living animals, such as mice. In such applications, an animal containing the bioluminescent cells is placed inside of the specimen chamber, and within the field of a photodetection device, such as an intensified CCD camera. The camera is then activated to detect the emitted photons. The photon signal may then be used to construct a luminescent image of photon emission. The luminescent image is constructed without using light sources other than the luminescence from the sample itself. This luminescence is recorded as a function of position to produce the luminescence image. The photographic image may also be taken of the same sample to aid in position visualization of the luminescent image. One approach to generating such composite photographic/luminescence images is described in U.S. Pat. No. 5,650,135 issued to Contag et al. on Jul. 22, 1997. The entire disclosure of that patent is incorporated herein by reference for all purposes.

Figure 4:
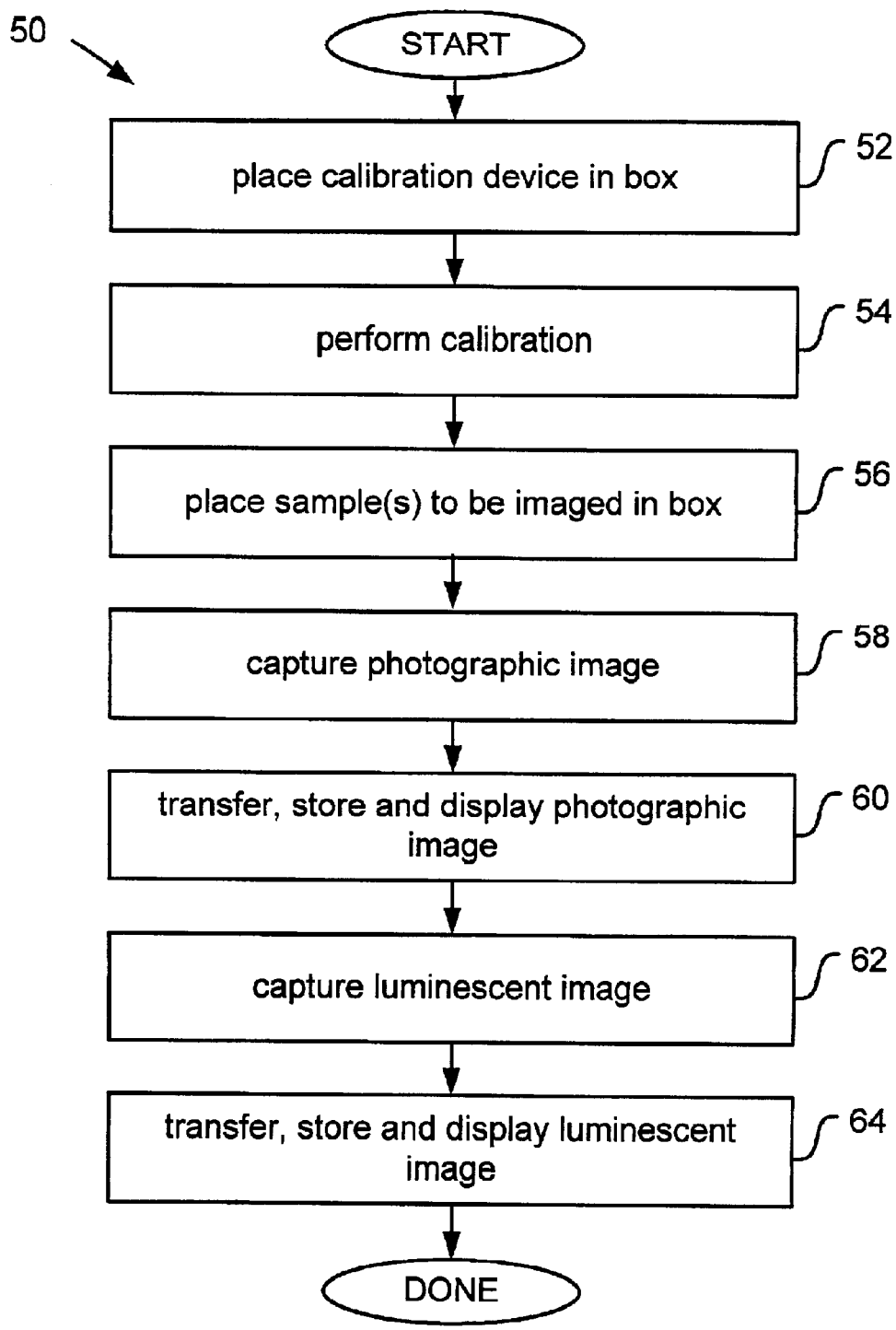
FIG. 4 is a flow chart illustrating a method of using the imaging box of FIG. 1 in accordance with embodiments of the invention.

Turning now to FIG. 4, a flow chart illustrates a method of using imaging system 10 of FIG. 1 and calibration device 70 in accordance with one embodiment of the invention. The method begins by placing calibration device 70 in box 12, and within the field of a photodetection device, such as an intensified CCD camera (52). The calibration device 70, imaging box 12 and its associated imaging components are then used to calibrate the light capture components of system 10 such as the camera and imaging box 12, and one or more parameters associated with image capture using system 10, such as the spatial and spectral characteristics of camera 20 (54), as described in further detail below and with respect to FIG. 5.

After calibration and removal of the calibration device, a sample or specimen may be placed on a stage in imaging box 12 (56). Imaging box 12 and associated image components may then be prepared for capturing a photographic image of the sample. The preparation may include launching imaging and acquisition software (e.g., "LivingImage", Xenogen Corporation, Alameda, Calif.) on the computer 28 and initializing the camera 20. Further preparations may include selecting a desired stage position is a moveable stage is used, closing the door to box 12, activating the photographic capture option in the software, and turning on the lights in the box. Preparations may further include focusing the lens, selectively positioning an appropriate lens filter, setting the f-stop, etc.

The photographic image is then captured (58). In one embodiment, a "live mode" is used during photographic imaging of the sample to observe the sample in real time. The live mode includes a sequence of photographic images taken frequently enough to simulate live video. Upon completion of photographic capture, the photographic image data are transferred to an image processing unit 26 and/or computer system 28 (60). These may be used to manipulate and store the photographic image data as well as process the data for display on computer monitor 38.

Subsequently, imaging box 12 and associated image components are prepared for luminescence image capture. Such preparation may include, for example, selecting luminescent exposure time and binning level using the computer 28, and turning off the lights in the cavity 44. The CCD camera 20 then captures (62) the luminescence image over a set period of time (up to several minutes). The luminescence image data are transferred to the image processing unit 26 and/or computer 28 (64), which may be used to manipulate and store the luminescence image data as well as process it for display on the computer display 38. The manipulation may also include overlaying the luminescent image with the photographic image and displaying the two images together as an "overlay" image, with the luminescence data typically shown in pseudocolor to show intensity. At this point, the user has the components of a digital overlay image (including the luminescence image and the photographic image) stored in the computer 28. The information contained in these image may be analyzed and manipulated as desired.

IV. Calibration

Figure 5:
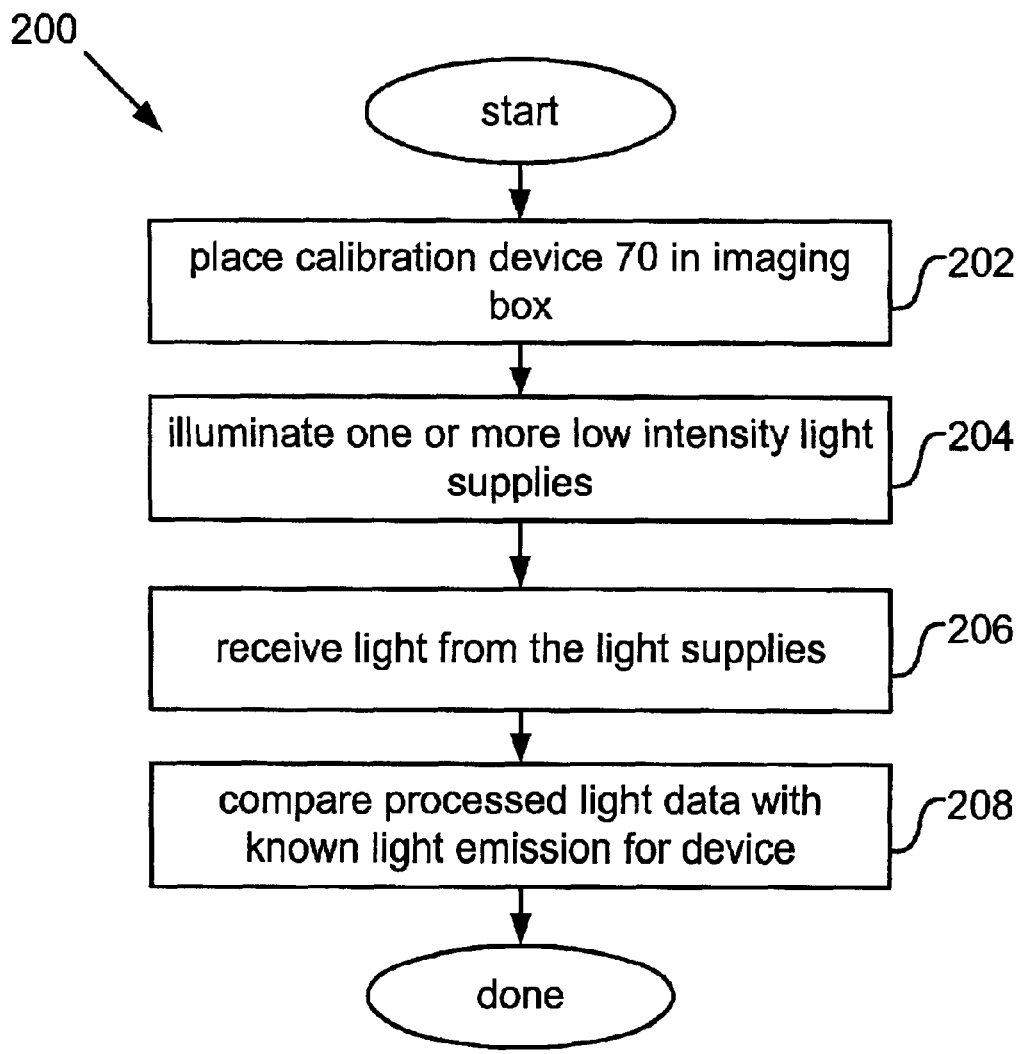
FIG. 5 illustrates a process flow for calibrating a low-level light imaging system in accordance with one embodiment of the present invention.

FIG. 5 illustrates a process flow 200 for calibrating a low-level light imaging system in accordance with one embodiment of the present invention. The imaging system is capable of capturing an image of a low intensity light source, on the order of individual photons, for example.

Process flow 200 begins by placing a light calibration device, such as that described with respect to FIG. 3, in an imaging box (202). The light calibration device includes an array of low intensity light supplies. Each low intensity light supply may be illuminated using a suitable electrical switch in conjunction with a light source operably coupled to one or more of the low intensity light supplies (204).

A camera receives the light emitted from the calibration device (206) and provides a signal representative of the emitted light to an associated image processing system. This may include photographic and/or luminescent image capture, and may include steps for each as described above with image capture of a sample in process flow 50. In one embodiment, calibration device 70 is used to assess the ability of the imaging box to seal light. In this case, light is received and processed from the low intensity light supplies for an extended period of time, long enough to assess the light integrity of the imaging box. For example, light received in the range of about 1 second to about 5 minutes may be suitable for some imaging boxes.

The image processing system processes the light emission data and compares the processed light data with known light emission for device 70 (208). In one embodiment, processing the light emitted from the calibration device comprises integrating the amount of light in photons received over time. Since the device may be designed to emit a known value for light per unit time produced from each light supply, a comparison of the number of photons received by the imaging system with the number of photons produced from the calibration device gives a user a simple comparison for assessing imaging system accuracy. In one embodiment, the light sources are calibrated to absolute units, e.g., against a known radiance standard. For example, the light sources may be calibrated to a National Institute for Standards and Technology (NIST) traceable OL Series 425 Integrating Sphere available from Optronic Laboratories of Orlando, Fla. In this case, a calibration regime is provided at intervals that will be denoted on sticker 83.

Figure 6:
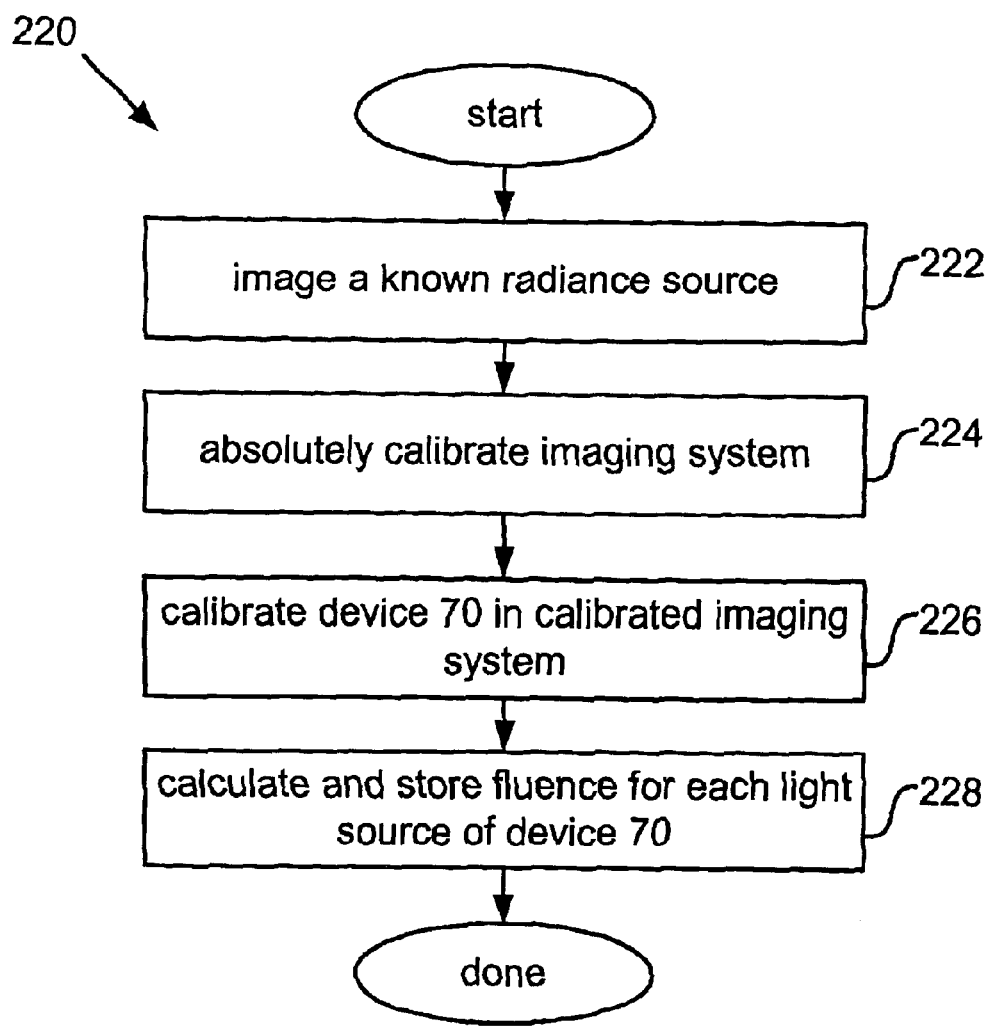
FIG. 6 illustrates a process flow for cross calibrating the calibration device of FIGS. 2A–2B against a known intensity light source in accordance with a specific embodiment of the present invention.

FIG. 6 illustrates a process flow 220 for cross calibrating device 70 against a known intensity light source in accordance with a specific embodiment of the present invention. Process flow 220 begins by inserting a device with a known radiance, such as the 425 Integrating Sphere mentioned above, within an imaging system such as imaging system 10 (222). This is done to calibrate the imaging system to known or absolute levels, and may include calculating conversion factors from analog to digital units (or counts) as received by the camera to radiance associated with imaging system 10 (224), as one of skill in the art will appreciate. Once the calibrating imaging system has been calibrated to known levels, it may be used to calibrate device 70. This comprises inserted device 70 into the box (226) and determining the fluence (228) for each light source. The fluence for each light source is then noted on sticker 83 attached to faceplate 72 to provide the light calibration information for each light supply 74. For example, the information may include absolute photon emission over time, e.g. the number of photons per second, for each light supply 74.

In some cases, measures may be taken to increase radiometric stability of the light sources over time. In a specific embodiment, a light source includes a self-monitoring photodiode and uses external components to monitor the diode's light output. In this manner, the light output from the diode can be held substantially constant. To further improve radiometric stability over time, a battery level sensing circuit may be employed that denies the diode a supply voltage if the battery power level may undesirably effect diode light output. In this manner, light source stability remains substantially consistent for a long period of time, e.g., months to a year.

While digital cameras output raw image data in "analog digitizer units" (ADU) or "counts", the terms are substantially equivalent for calibration purposes herein. Counts are uncalibrated units that refer to the amplitude of the signal detected by the digitizer incorporated into the CCD camera. The number of counts detected by the digitizer is proportional to the number of photons incident on a given CCD pixel, and process flow may be used to provide a proportionality constant that varies from camera to camera and system to system. Alternately, image data may be processed and calibrated according to a processing state associated with output on a display, or another processing state associated with image analysis. For example, photons/sec/cm2/sr, where sr refers to steradian, are units of photon radiance on a surface, which may be used for calibration. This mechanism of measurement describes the amount of light energy captured by the lens. As a result of process flow 200, the measurements in units of radiance have already taken into account settings such as integration time, binning, f/stop, and field-of-view. A distinction between absolute physical units and relative units of "counts" discussed above is that the radiance units refer to light emission from the animal or calibration device itself, as opposed to counts which refers to light emission incident on the detector.

Calibration according to process flow 200 may be flexibly applied. In some cases, process flow 200 is repeated periodically over the operational life of the imaging system, e.g., once every couple of months, to verify the operational integrity of the system over time. Obtaining an absolute performance of the imaging system according to process flow 200 is particularly useful, for example, for normalizing imaging data received from a sample. So if a user were to take several images (during a single session) of an animal with different integration times or different fields-of-view, the displayed images would all have the same signal amplitude because the radiance on the surface of the animal is not changing—only the camera settings are changing. Basically, the camera settings have been calibrated out. The advantage to the user is that camera settings can now be changed during the course of an experiment and there is no need to make any adjustments to the images or the measured image data. The other advantage of absolute physical units is that images or image data can now be compared quantitatively between different camera systems at, possibly, different facilities.

While this invention has been described in terms of several preferred embodiments, there are alterations, permutations, and equivalents which fall within the scope of this invention which have been omitted for brevity's sake. For example, although the light interface components of FIG. 3B are illustrated in a particular order that the light encounters them, it is understood that other designs may vary the order of the components described herein. In addition, although the light supplies 74 are illustrated and described each with a dedicated light source, it is understood that multiple light supplied may share a light source. It is therefore intended that the scope of the invention should be determined with reference to the appended claims.

What is claimed is:

1. A calibration device capable of producing light for calibrating a low light level imaging system, the device comprising:

an array of low intensity light supplies for emitting light in the range of about $10^3$ to about $10^8$ photons/second/centimeter squared/steradian, wherein each low intensity light supply comprises a light interface for receiving light from a light source and for emitting at least a portion of the light from the device;

a housing that contains the array of low intensity light supplies; and a voltage source, in electrical communication with the light source for each low intensity light supply, and designed or configured to provide power to the light source.

2. The device of claim 1 wherein the light source is a light emitting diode.

3. The device of claim 1 wherein the light from each light source is substantially constant over the operating life of the calibration device.

4. The device of claim 3 wherein the light source is a self-monitoring low intensity diode.

5. The device of claim 3 further comprising a voltage regulator in electrical communication with the voltage source.

6. The device of claim 1 wherein the light interface comprises an opaque diaphragm with a light transmission hole disposed along a light path between the light source for a low intensity light supply and emission of light from the light source from the device.

7. The device of claim 4 wherein the hole has a diameter in the range of about 30 to about 100 microns.

8. The device of claim 7 wherein each low intensity light supply is designed or configured to emit light from the interface in the range of about $10^5$ to about $10^7$ photons/second/centimeter squared/steradian.

9. The device of claim 1 further comprising a voltage shutoff in electrical communication with the voltage source.

10. The device of claim 1 further comprising a status indicator in electrical communication with the voltage source that temporarily flashes to indicate operation of the device.

11. The device of claim 1 wherein the array of low intensity light supplies comprises from 2 and 8 light supplies in the array.

12. The device of claim 1 wherein the height of the device is designed relative to the average height of a surface of a specimen to be imaged.

13. The device of claim 12 wherein the light source for a low intensity light supply in the array is configured to emit light horizontally towards the light interface.

14. The device of claim 13 further including an opaque surface disposed along a light path between the light source for a low intensity light supply and emission of light from the light source from the device, the opaque surface for deflecting a portion of the horizontal light vertically.

15. The device of claim 1 wherein the light interface comprises a light diffuser disposed along a light path between the light source for a low intensity light supply and emission of light from the light source from the device, the light diffuser creating a Lambertian distribution for a low intensity light supply in the array.

16. The device of claim 1 wherein the light source for a low intensity light supply in the array produces one of red and green light.

17. The device of claim 1 further comprising a neutral density filter disposed along a light path between the light source for a low intensity light supply and emission of light from the light source from the device, the neutral density filter being attenuating light transmitted through the filter.

18. The device of claim 1 wherein the device is substantially light tight.

19. The device of claim 1 wherein each of the low intensity light supplies is calibrated to absolute units.

20. A system for capturing an image of a low intensity light source with a camera, the system comprising:

an imaging box having a set of walls enclosing an interior cavity and a camera mount configured to position the camera relative the interior cavity;

a calibration device comprising a voltage source and an array of low intensity light supplies for emitting light in the range of about $10^3$ to about $10^8$ photons/second/centimeter squared/steradian, wherein each low intensity light supply comprises a light interface for receiving light from a light source and for emitting at least a portion of the light from the device, the voltage source being in electrical communication with the light source for each low intensity light supply; and a processor designed or configured to receive image data corresponding to light emitted from the calibration device and compare the image data to known light emission data for the calibration device.

21. The system of claim 20 wherein the imaging box is substantially light tight.

22. The system of claim 20 wherein the light interface comprises a light diffuser disposed along a light path between the light source for a low intensity light supply and emission of light from the light source from the device, the light diffuser designed or configured to diminish directionality of the light produced by the light source for a low intensity light supply in the array.

23. The system of claim 20 further comprising a neutral density filter disposed along a light path between the light source for a low intensity light supply and emission of light from the light source from the device, the neutral density filter being designed or configured to attenuate light transmitted through the filter.

24. A method for calibrating a system capable of capturing an image of a low intensity light source, the system comprising an imaging box and a camera for capturing the image, the method comprising:

placing a light calibration device in the imaging box, the light calibration device including an array of low intensity light supplies;

emitting light from one or more of the low intensity light supplies in the range of about $10^3$ to about $10^8$ photons/second/centimeter squared/steradian;

receiving the light from the one or more of the low intensity light supplies using the camera; and comparing the received light with a known light emission for the one or more of the low intensity light supplies.

25. The method of claim 24 further comprising constructing a photographic image using the light received.

26. The method of claim 25 further comprising constructing a luminescent image using the light received.

27. The method of claim 26 further comprising comparing the spatial resolution between the luminescent image and the photographic image.

28. The method of claim 24 wherein receiving the light from the one or more of the low intensity light supplies occurs for an extended period of time long enough to assess the light integrity of the imaging box.

29. The method of claim 28 wherein receiving the light emissions for each of the one or more of the low intensity light supplies occurs in the range of about 1 second to about 5 minutes.

30. The method of claim 24 wherein comparing the received light with the known light emission comprises provides a spectral assessment for the imaging system.

* * * * *